(12) United States Patent
Buckberry et al.

(10) Patent No.: US 10,543,305 B2
(45) Date of Patent: Jan. 28, 2020

(54) METHOD OF HEAT SANITIZATION OF A HAEMODIALYSIS WATER CIRCUIT USING A CALCULATED DOSE

(71) Applicant: Quanta Fluid Solutions Limited, Warwickshire (GB)

(72) Inventors: Clive Buckberry, Warwickshire (GB); Keith Heyes, Warwickshire (GB); Eduardo Esser, Warwickshire (GB)

(73) Assignee: Quanta Dialysis Technologies Limited, Alcester, Warwickshire (GB)

( * ) Notice: Subject to any disclaimer, the term of this patent is extended or adjusted under 35 U.S.C. 154(b) by 167 days.

(21) Appl. No.: 15/315,114

(22) PCT Filed: Jun. 2, 2015

(86) PCT No.: PCT/GB2015/051610
§ 371 (c)(1),
(2) Date: Nov. 30, 2016

(87) PCT Pub. No.: WO2015/185920
PCT Pub. Date: Dec. 10, 2015

(65) Prior Publication Data
US 2017/0197020 A1    Jul. 13, 2017

(30) Foreign Application Priority Data
Jun. 2, 2014  (GB) .................................. 1409796.8

(51) Int. Cl.
*A61M 1/16*    (2006.01)
*C02F 1/02*    (2006.01)
(Continued)

(52) U.S. Cl.
CPC ............. *A61M 1/1686* (2013.01); *A61L 2/04* (2013.01); *A61L 2/24* (2013.01); *A61M 1/1688* (2014.02);
(Continued)

(58) Field of Classification Search
CPC .............. A61M 1/1686; A61M 1/1688; A61M 2205/12; A61M 2205/28;
(Continued)

(56) References Cited

U.S. PATENT DOCUMENTS 5,591,344 A * 1/1997 Kenley ...................... A61L 2/04
                                                   210/636
5,665,307 A * 9/1997 Kirschner ............. A61L 2/0088
                                                   422/28
(Continued)

FOREIGN PATENT DOCUMENTS

DE    29 34 167 A1    3/1981
WO    WO 96/25214    8/1996
(Continued)

OTHER PUBLICATIONS

Aug. 28, 2015, International Search Report for PCT/GB2015/051610.
(Continued)

*Primary Examiner* — Joseph W Drodge
(74) *Attorney, Agent, or Firm* — Hahn Loeser & Parks, LLP

(57) ABSTRACT

A method of sanitizing liquid for use in a medical device, the method comprising the steps of providing a medical device defining a water circuit with a volume of liquid, sensing the temperature of the volume of liquid with a sensor, heating the volume of liquid from an initial temperature to exceed a threshold temperature, maintaining the volume of liquid above the threshold temperature, determining a time-temperature value for the volume of liquid periodically once the threshold temperature has been exceeded, calculating a cumulative time-temperature value and providing an output signal once the cumulative time-temperature value has
(Continued)

reached a level indicative of a sanitizing dose. A medical device and a liquid sanitizer are also disclosed.

27 Claims, 5 Drawing Sheets

(51) Int. Cl.
    *A61L 2/04*     (2006.01)
    *A61L 2/24*     (2006.01)
    *C02F 1/00*     (2006.01)
    *C02F 103/02*     (2006.01)

(52) U.S. Cl.
    CPC ............... *C02F 1/008* (2013.01); *C02F 1/02* (2013.01); *A61L 2202/14* (2013.01); *A61L 2202/22* (2013.01); *A61M 2205/18* (2013.01); *A61M 2205/3368* (2013.01); *A61M 2205/50* (2013.01); *A61M 2205/581* (2013.01); *A61M 2205/583* (2013.01); *C02F 2103/026* (2013.01); *C02F 2209/02* (2013.01); *C02F 2209/44* (2013.01); *C02F 2303/04* (2013.01)

(58) Field of Classification Search
    CPC ...... A61M 2205/3368; A61M 2205/36; A61M 2205/3653; A61M 2205/50; A61M 2205/581; A61M 2205/583; A61L 2/04; A61L 2/24; A61L 2202/02; A61L 2/14; B01D 61/28; B01D 61/30; B01D 61/32; B01D 65/02; B01D 65/022; B01D 2313/38; B01D 221/32; B01D 2321/32; C02F 1/008; C02F 1/02; C02F 2103/026; C02F 2303/04; C02F 2209/005; C02F 2209/02
    USPC ..... 210/149, 175, 186, 646, 742; 422/28, 38; 604/4.01, 5.01, 6.09, 6.13
    See application file for complete search history.

(56) References Cited

U.S. PATENT DOCUMENTS

| | | | | |
|---|---|---|---|---|
| 5,948,247 | A * | 9/1999 | Gillerfalk | A61M 1/1688 210/175 |
| 6,663,829 | B1 * | 12/2003 | Kjellstrand | A61J 1/2093 206/219 |
| 6,967,002 | B1 * | 11/2005 | Edgson | A61L 2/0023 210/143 |
| 2003/0217962 | A1 * | 11/2003 | Childers | A61M 1/28 210/258 |
| 2004/0215129 | A1 | 10/2004 | Edgson et al. | |
| 2008/0283096 | A1 * | 11/2008 | Scheringer | A61G 9/02 134/18 |
| 2009/0012450 | A1 * | 1/2009 | Shah | A61L 2/183 604/29 |
| 2010/0263687 | A1 * | 10/2010 | Braun | A47L 15/0002 134/18 |
| 2012/0308431 | A1 * | 12/2012 | Kotsos | A61M 1/1686 422/3 |

FOREIGN PATENT DOCUMENTS

| | | |
|---|---|---|
| WO | WO 00/57935 | 10/2000 |
| WO | WO 2014/082855 A1 | 6/2014 |

OTHER PUBLICATIONS

Aug. 28, 2015, Written Opinion of International Searching Authority for PCT/GB2015/051610.

\* cited by examiner

METHOD OF HEAT SANITIZATION OF A HAEMODIALYSIS WATER CIRCUIT USING A CALCULATED DOSE

The present application is a submission under 35 USC § 371 of international application no. PCT/GB2015/051610, filed 2 Jun. 2015 and published in the English language with publication number WO 2015/185920 A1 on 10 Dec. 2015, which claims the benefit of the filing date of GB 1409796.8, filed 2 Jun. 2014.

The present invention relates to the preparation of dialysis fluid for hemodialysis and related therapies and substitution fluid for use in online therapies, such as hemodiafiltration and hemofiltration. In particular, the present invention relates to a method for heat sanitization of a liquid used in one of the above processes.

It is known to use heat to destroy microorganisms. During a thermal destruction process, the rate of destruction of microorganisms is logarithmic, as is the rate of growth of the microorganisms. Thus bacteria subjected to heat are killed at a rate that is proportional to the number of organisms present. The process is dependent both on the temperature of exposure and the time required at this temperature to accomplish to desired rate of destruction.

Thermal calculations thus involve the need for knowledge of the concentration of organisms to be destroyed, the acceptable concentration of organisms that can remain behind (spoilage organisms, for example, but not pathogens), the thermal resistance of the target organisms (the most heat tolerant ones), and the time-temperature relationship required for destruction of the target organisms.

Disinfection of many water based systems in medical devices is frequently achieved by elevating the temperature for a stipulated period of time, thereby using heat to destroy the microorganism in the water. In dialysis it is common for a combination of 80 degrees Celsius (° C.) to be maintained for 30 minutes.

There are several well-established time-temperature relationships for moist heat disinfection which are regarded as equally acceptable. For moist heat disinfection a particular time at a particular temperature can be expected to have a predictable lethal effect against a standardised population of organisms. It is therefore possible to define a standard exposure which will yield a disinfected product in a correctly operated Washer Disinfector (WD). Actual exposures can then be related to these standard exposure conditions.

Definition of such disinfection processes may be achieved by means of the $A_0$ method which uses a knowledge of the lethality of the particular process at different temperatures to assess the overall lethality of the cycle and express this as the equivalent exposure time at a specified temperature.

The A value is a measure of the heat resistance of a microorganism.

A is defined as the equivalent time in seconds at 80° C. to give a disinfection effect.

The z value indicates the temperature sensitivity of the reaction. It is defined as the change in temperature required to change the A value by a factor of 10.

When the z value is 10° C., the term $A_0$ is used.

The $A_0$ value of moist heat disinfection process is the equivalent time in seconds at a temperature of 80° C. delivered by that process to the product with reference to microorganisms possessing a z value of 10° C.

$$A_0 = \sum 10^{[\frac{(T-80)}{z}]} dt$$

Where:
$A_0$ is the A value when z is 10° C.;
t is the chosen time interval, in seconds;
and T is the temperature in the load in ° C.

In calculating $A_0$ values a temperature threshold for the integration is set at 65° C. since for temperatures below 65° C. the z and D value of thermophillic organisms may change dramatically and below 55° C. there are a number or organisms which will actively replicate.

In dialysis current practice, raising the temperature to 80° C. for 30 minutes gives a benchmark value $A_0$ equal to 1800.

The present invention aims to provide an efficient method of heat sanitization of a haemodialysis water circuit.

According to the first aspect of the present invention, there is provided a method of sanitizing liquid for use in a medical device, comprising the steps of sensing the temperature of a volume of liquid with a sensor; heating the volume of liquid from an initial temperature to exceed a threshold temperature; maintaining the volume of liquid above the threshold temperature; determining a time-temperature value for the volume of liquid periodically once the threshold temperature has been exceeded; calculating a cumulative time-temperature value; and providing an output signal once the cumulative time-temperature value has reached a level indicative of a sanitizing dose.

Calculation of the time-temperature value for the volume of liquid based on the cumulative effect of heating the water provides a more accurate model of the sanitization process by ensuring a fixed dose of heat sanitization is applied to the volume of liquid. Furthermore, it maximises the benefits of high temperatures (in particular those above 80° C.) thereby reducing the time for which components are exposed to elevated temperatures. Natural variation in the control loop and water recirculation will cause natural temperature oscillations. Those time periods below 80° C. but above the minimum temperature range are integrated into the dose and those above are not leveraged according to the power law relationship.

The cumulative time-temperature value may be calculated by a processor. Alternatively, the cumulative time-temperature value may be calculated from a lookup table.

The method may comprise the further step of setting a target cumulative time-temperature value and providing the output signal once the target cumulative time-temperature value is reached.

The output signal may be in the form of an audible or visual alarm. This informs the user or operator that the sanitization process is complete.

The output signal may automatically cause termination of the liquid heating. This prevents the heat sanitization cycle from running for longer than is necessary.

The method may comprises the further step of maintaining the volume of liquid below an upper temperature. This may be to prevent boiling of the sanitizing liquid, or prevent unnecessary thermal stress on the components of the heat sanitization device.

The method may comprise the further step of setting the threshold temperature. The method may comprise the further step of setting an overall heating time. This allows the process to be tailored according to the environmental conditions (for example room temperature, liquid input temperature) the situational conditions, (for example emergency procedure, routine procedure, clinic timetables) and the patient's needs. Thus the time and/or temperature may be selected without compromising the dose of heat sanitization applied to the volume of liquid.

The threshold temperature may be between 55° C. and 65° C.

The upper temperature may be between 70° C. and 99° C.

Multiple temperature sensors may be used to provide the temperature of the volume of liquid.

In one embodiment, the cumulative time-temperature value may be calculated according to $$A_0 = \sum 10^{[\frac{(T-80)}{z}]} dt$$

Where:

$A_0$ is the A value when z is 10° C.;

t is the chosen time interval, in seconds;

and T is the temperature in the load in ° C.

This allows the destruction of organisms at 65° C. to 80° C. to be included in the calculation of the cumulative time-temperature value.

The $A_0$ value may be equal to 1800.

According to a second aspect of the present invention, there is provided a liquid sanitizer comprising a tank containing a volume of liquid; a sensor arranged to sense the temperature of the volume of liquid; a heater arranged to heat the volume of liquid from an initial temperature to exceed a threshold temperature, and maintain the volume of liquid above the threshold temperature; and a processor, wherein the processor is configured to determine a time-temperature value for the volume of liquid periodically once the threshold temperature has been exceeded and calculate a cumulative time-temperature value so as to provide an output signal once a cumulative time-temperature value indicative of a sanitizing dose is reached.

The processor may be programmable to alter at least one of the threshold temperature and the cumulative time-temperature value.

According to a third aspect of the present invention, there is provided a dialyser incorporating the liquid sanitizer according to the second aspect of the present invention.

An embodiment of the present invention will now be described, by way of example only, with reference to the accompanying figures, in which.

Figure 1:
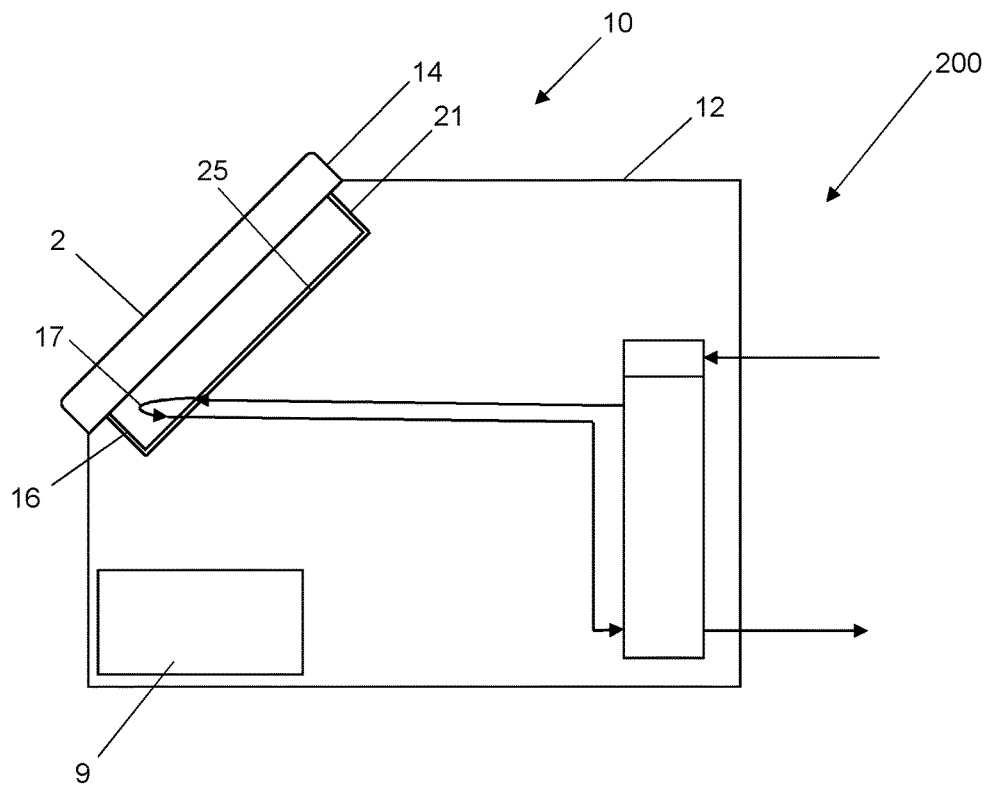
FIG. 1 is a schematic of a dialysis machine incorporating the liquid sanitizer.

Referring to FIG. 1, a dialysis machine 10 is shown having a main body 12 and a hinged door 14. The door 14 is hinged so as to allow a dummy dialysis cartridge 16 to be received between the main body 12 and the door.

The machine 10 has a blood pumping portion indicated generally at 9 for pumping patient blood to and from a dialyser (not shown for clarity) in a known manner. The main body 12 has a platen 21 behind which is an engine portion (not shown for clarity). The platen 21 is configured to receive the dummy cartridge 16 within a recessed portion 25.

The engine portion includes a pneumatic pump for providing pressure and vacuum to operate the machine and a controller to control retention of the dummy cartridge 16 within the machine 10 and fluid flow on the dummy cartridge 16 as will be discussed in further detail below.

The door 14 has an outer side including a user interface 2. The door 14 includes an actuator in the form of an airbag (not shown), operable by the engine portion to provide a closure load to close the dummy cartridge 16 onto the platen 21 and to ensure that a continuous seal fully engages the dummy cartridge 16.

The dummy cartridge 16 will now be described in further detail. The dummy cartridge 16 has a chassis defining a door side and a platen side. In use the platen side of the cartridge 16 engages the platen 21 on the main body 12 of the machine 10, and the door side engages an interface plate (not shown) on the door 14 of the machine 10.

The dummy cartridge 16 is formed from an acrylic such as SG-10 which is moulded in two parts (a platen side and a patient side) before being bonded together to form the chassis. Both the platen side and door side are covered in a clear flexible membrane formed from, for example, DEHP-free PVC which is operable by pneumatic pressure applied to the membrane by the pneumatic compressor in the main body via the platen 21. In this way a series of flow paths 17 are formed in the cartridge for carrying sanitizing water.

In use, the engine portion of the machine 10 applies either a positive or negative pressure to the membrane via the platen 21 in order to selectively open and close valves and pumps to pump sanitizing fluid through the dummy cartridge 16, which is described in detail below.

The machine 10 has liquid sanitizer generally designated as 200. The arrows on FIG. 1 show the sanitizing water flow path when the liquid sanitizer is in use.

Figure 2:
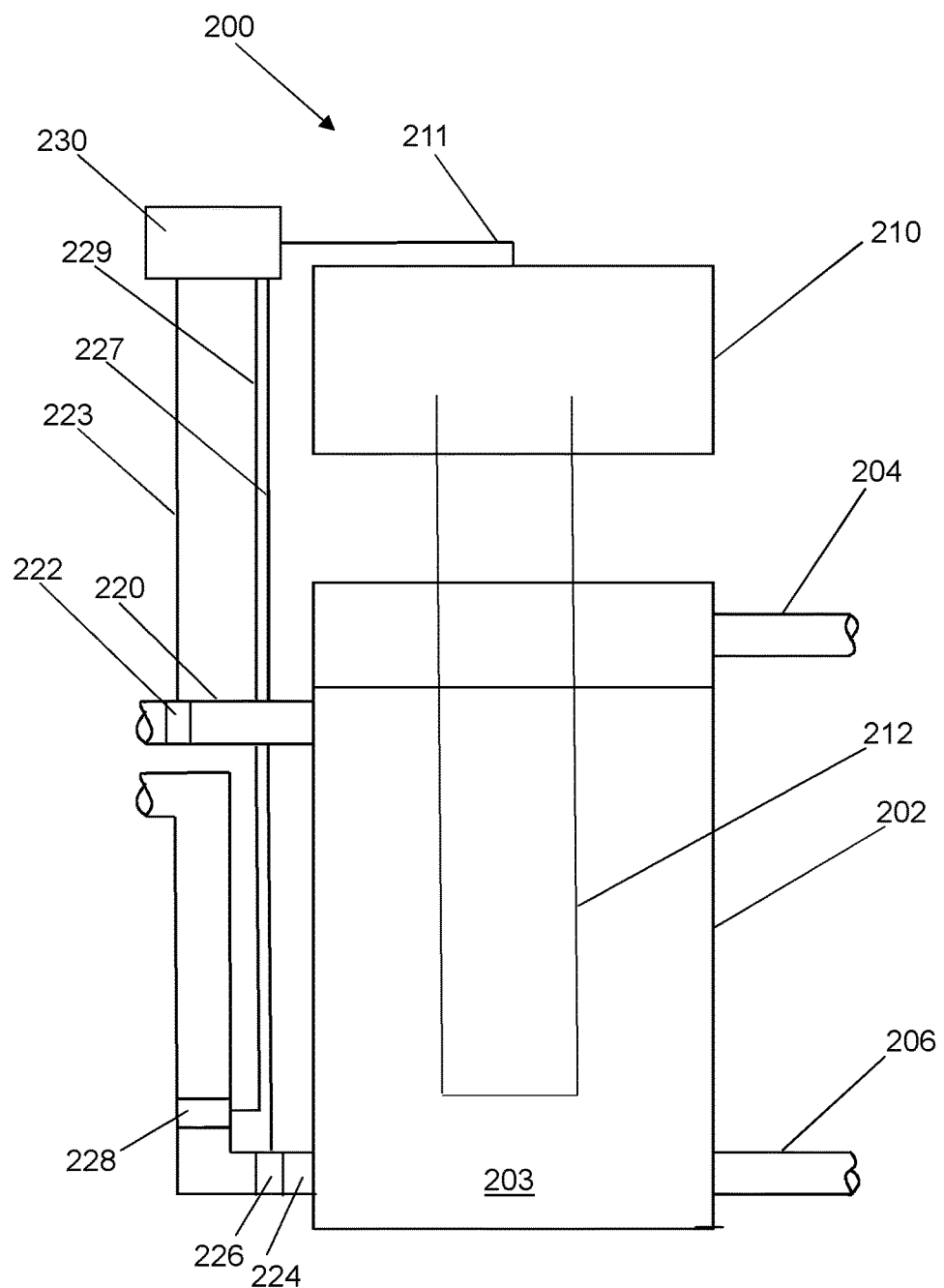
FIG. 2 is a magnified detail view of the liquid sanitzer of FIG. 1.

With reference to FIG. 2, the liquid sanitizer will be described in further detail.

The liquid sanitizer 200 has a tank 202, a heater 210 and a processor 230. The tank 202 contains, in use, a volume of water 203.

The tank 202 has an inlet 204 and a drain 206. The inlet 204 is connectable to a water source (not shown) and the drain 206 is connectable to a waste pipe (also not shown). The tank 202 also has a feed pipe 220 connectable to the dummy cartridge 16 via the platen 21 and a return pipe 224, also connectable to the dummy cartridge 16 via the platen 21. Referring back to FIG. 1, the dummy cartridge 16 has a sanitizing water circulation path 17 so as to complete a sanitizing water circuit comprising the tank 202, feed pipe 220, dummy cartridge 16 and return pipe 224.

The heater 210 has a heating element 212 arranged to heat the volume of water 203 contained within the tank 202, in this case by immersion in the volume of water 203 in the tank 202. The heater 210 is electronically connected to processor 230 by heater connector 211.

Temperature sensors are arranged on the sanitizing water circuit. A driver temperature sensor 222 is arranged on the feed pipe 220 adjacent the water tank 202. A return temperature sensor 226 is arranged on the return pipe 224 adjacent the water tank 202. A check temperature sensor 228 is arranged on the return pipe adjacent, but offset from, the return temperature sensor 226. All three temperature sensors are electronically connected to the processor 230 via sensor connectors. Driver temperature sensor 222 is electronically connected to processor 230 by sensor connector 223. Return temperature sensor 226 is electronically connected to processor 230 by sensor connector 227. Check temperature sensor 228 is electronically connected to processor 230 by sensor connector 229.

The electronic connectors 211, 223, 228, 229 may be wired or wireless. The processor 203 may be remote to both the tank 202 and heater 210.

The processor 230 thereby controls both the heating of the water and receives the temperature values for the sanitizing water circuit.

In use, the tank 202 of liquid sanitizer 200 is filled with the desired quantity of water via inlet 204. This would typically be 500 ml, which is the amount sufficient to flush out the water circuit of a kidney dialyser.

The liquid sanitizer is then turned on. The processor 230 activates the heater 210 to heat the volume of water via the heating element 221 and the pump draws the water around the sanitizing water circuit. The temperature of the water exiting the tank 202 via feed pipe 220 is periodically sensed by drive temperature sensor 222, and the temperature data is periodically sent to processor 230 via sensor connector 223. The temperature of the water returning to the tank 202 via return pipe 224 is periodically sensed by return temperature sensor 226, and the temperature data is periodically sent to processor 230 via sensor connector 227. The processor 230 therefore periodically receives sensed temperature data to provide a feedback loop to moderate the heating of the volume of water 203 to maintain the temperature of the volume of water 203 above a threshold temperature.

When the processor 230 receives data from the sensor 220 that the volume of water 203 has exceeded the threshold temperature, the processor 230 periodically samples the temperature of the volume of water via the return temperature sensor 226, which theoretically represents the lowest possible temperature of the water on the sanitizing water circuit.

The value is checked by periodically sampling the temperature of the volume of water via the check temperature sensor 228.

The sampling is performed periodically at, for example, 1 second intervals. The sampling intervals may be varied as appropriate.

Each sampled temperature represents a time-temperature value, which can be calculated by the processor 230, or alternatively generated by a look-up table.

The processor 230 calculates a cumulative time-temperature value for the volume of liquid 20 by summing the sampled time-temperature values. This is compared to a target total time-temperature value indicative of a sanitizing dose.

Once the calculated cumulative time-temperature value and the target cumulative time-temperature value are equal, the processor 230 sends an output signal to indicate that a sanitizing dose has been reached. The output signal is received by the heater and automatically switches off the heater 210.

In an alternate embodiment, the processor 230 may switch off the water heater 210 in advance of a sanitizing dose being reached, by calculating that there is sufficient thermal energy contained within the water circuit that the water temperature will remain above the threshold temperature for long enough to ensure a sanitizing dose is reached. In that case, periodic sampling would be continued, such that the processor 230 is able to send the output signal to indicate that a sanitizing dose had indeed been reached.

The output signal is received by the LCD display unit, which displays the text "COMPLETE" in reference to the completed sanitizing dose. In alternate embodiments, the LCD display unit includes an audible alarm. The audible alarm can be configured to bleep repeatedly until the sanitizer is turned off.

Figure 3:
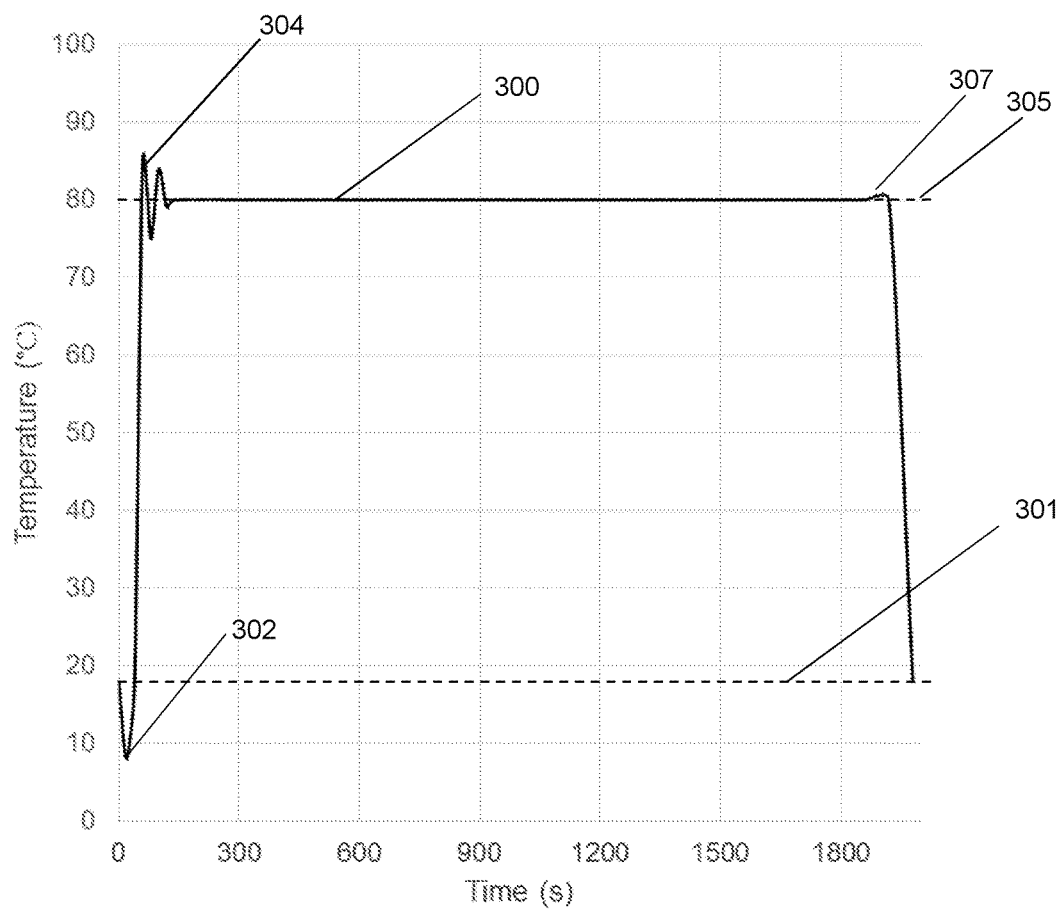
FIG. 3 is a temperature profile of the liquid in a liquid sanitizer undergoing a typical sanitization cycle.

With reference to FIG. 3, a typical temperature profile 300 of the water in a known liquid sanitizer is shown during a single disinfection cycle.

The water already contained within the tank is at room temperature 301 (18° C.) initially. As cool fresh water is added from a tap to ensure the correct quantity of water is provided in the tank (wherein the cool fresh water is typically 8° C.), the overall temperature of the liquid will drop slightly 302.

The water temperature then rises substantially linearly towards the target temperature of 80° C. 305, which is reached at about 60 seconds. There is a slight oscillation 304 of about one and a half wavelengths where the water temperature exceeds and passes below 80° C. (to approximately 85° C. and 75° C. respectively) as the water heater finds the correct balance to maintain a constant water temperature of 80° C. After approximately 30 minutes at 80° C. the water heater is switched off 307 and the water temperature steadily decreases to room temperature (18° C.) 301.

Figure 4:
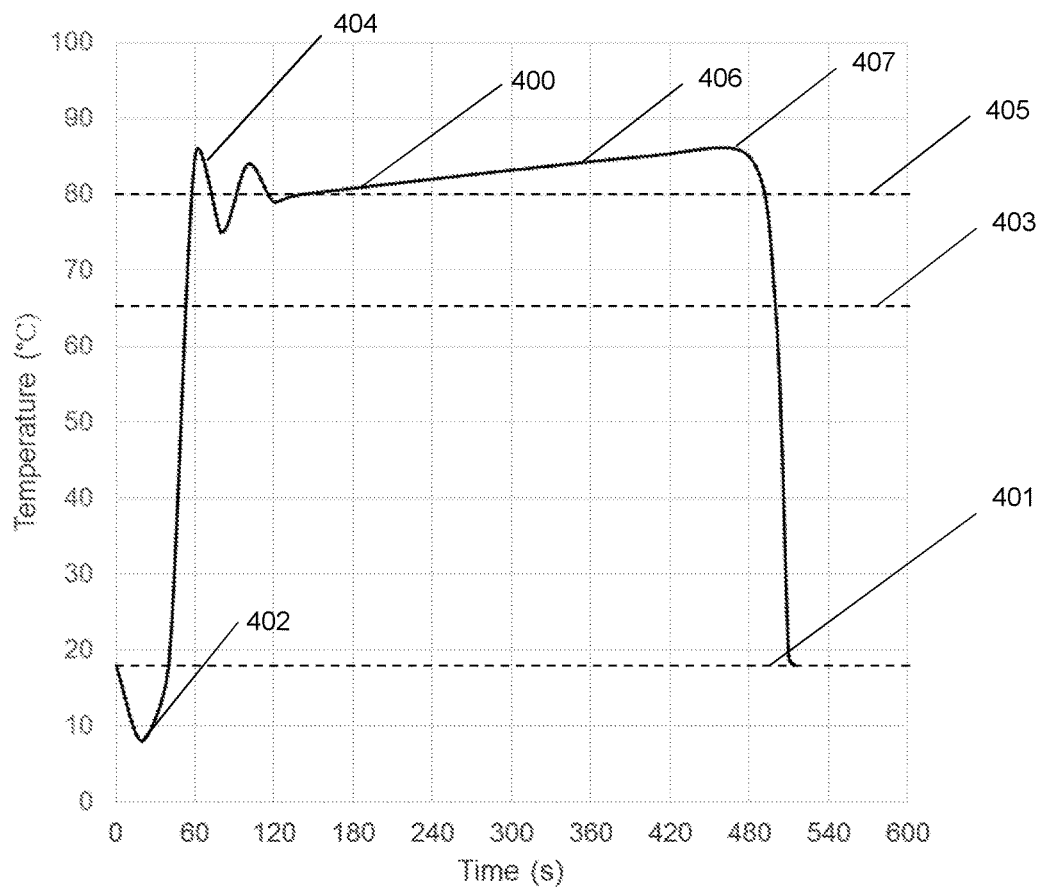
FIG. 4 is a temperature profile of the liquid in the liquid sanitizer of FIG. 1 undergoing a typical sanitization cycle.

With reference to FIG. 4 a typical temperature profile 400 of the water in the liquid sanitizer 200 is shown during a single disinfection cycle.

Similar notable points on the temperature profile are given similar reference numerals as that for FIG. 3, prefixed by a "4" instead of a "3" to indicate that they represent the temperature profile 400 of the water in the liquid sanitizer 200.

The initial drop in temperature 402 from room temperature 401 (18° C.) and subsequent heating of the water occurs following a similar time-temperature profile to that shown in FIG. 3.

However, when the temperature of the water exceeds the threshold temperature. 65° C. 403, the liquid sanitizer begins to record a time-temperature value.

Furthermore, when the target temperature 80° C. 405 is reached, the water temperature is continually raised 406 such that a greater time-temperature value contribution can be achieved with each sample.

The heater is switched off 407 after less than 8 minutes as there is sufficient thermal energy within the water to ensure that a complete sanitizing dose is achieved before the temperature of the water falls below the threshold temperature of 65° C. 403.

The overall cycle time for the sanitizing dose is slightly more than 8 minutes. This compares to the overall cycle time for a sanitizing dose according to the temperature profile of FIG. 3 of over 30 minutes.

An exemplary Lookup Table may include the following values for 1 second sampled increments:

TABLE 1

| Lookup Table | |
|---|---|
| Temperature (° C.) | Time-temperature value |
| 95 | 35.481 |
| 94 | 28.184 |
| 93 | 22.387 |
| 92 | 17.783 |
| 91 | 14.125 |
| 90 | 11.22 |
| 89 | 8.913 |
| 88 | 7.079 |
| 87 | 5.623 |
| 86 | 4.467 |
| 85 | 3.548 |

TABLE 1-continued

Lookup Table

| Temperature (° C.) | Time-temperature value |
|---|---|
| 84 | 2.818 |
| 83 | 2.239 |
| 82 | 1.778 |
| 81 | 1.413 |
| 80 | 1.122 |
| 79 | 0.891 |
| 78 | 0.708 |
| 77 | 0.562 |
| 76 | 0.447 |
| 75 | 0.355 |
| 74 | 0.282 |
| 73 | 0.224 |
| 72 | 0.178 |
| 71 | 0.141 |
| 70 | 0.112 |
| 69 | 0.089 |
| 68 | 0.071 |
| 67 | 0.056 |
| 66 | 0.045 |
| 65 | 0.035 |
| 64 | 0 |

Thus it can be seen that for each 1° C. increase in water temperatures above 80° C., the time-temperature contribution is significantly increased. Three seconds at 85° C. is equivalent to over 10 seconds at 80° C.

Figure 5:
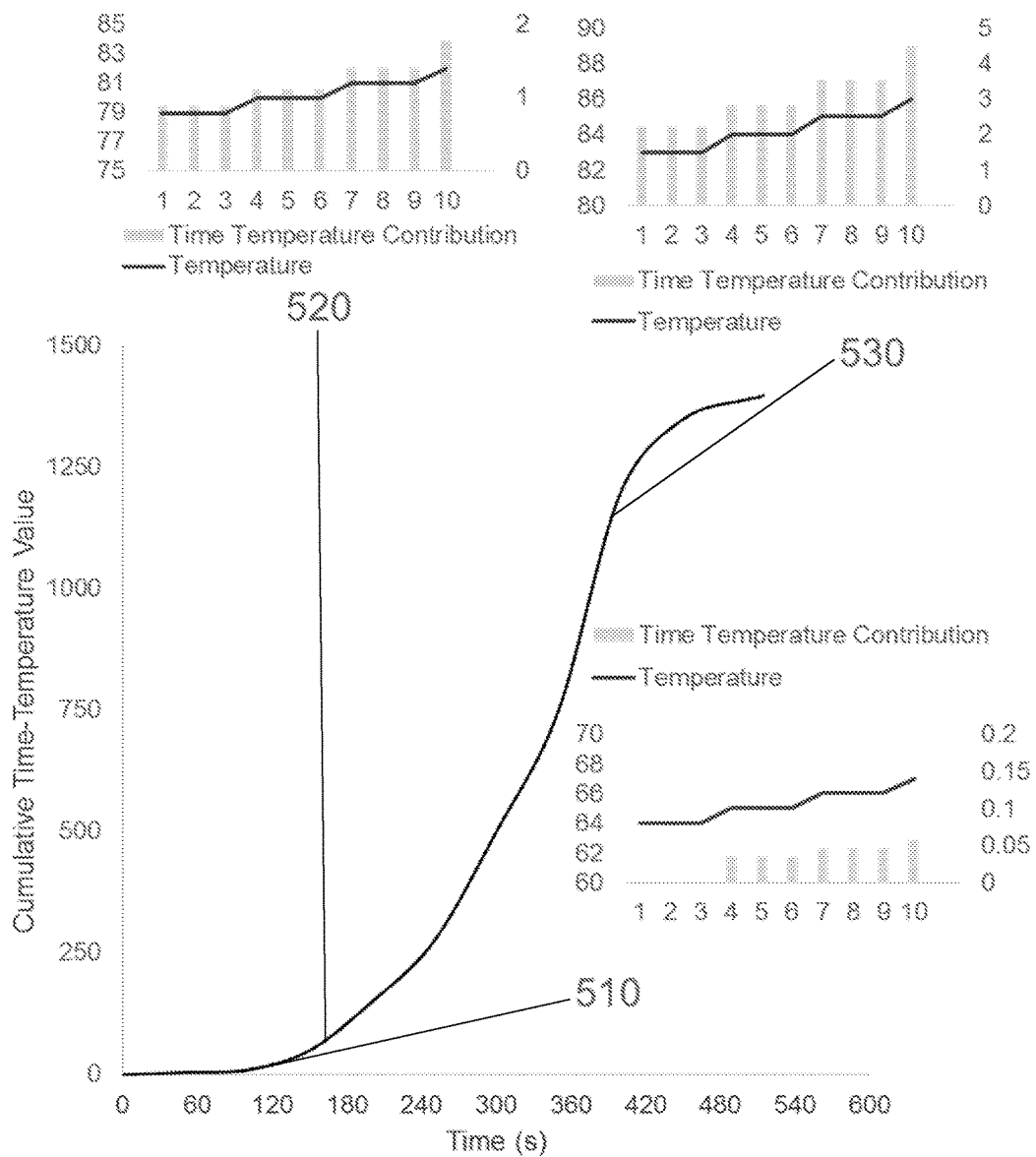
FIG. 5 shows the non-linear contribution to the cumulative time-temperature value, during a single sanitization cycle referred to in the typical temperature profile of FIG. 4.

In FIG. 5, the non-linear contribution to the cumulative time-temperature value, during the single disinfection cycle referred to in the typical temperature profile of FIG. 4, is shown in the main graph. The main graph has the cumulative time temperature value on the Y-axis, and the cycle time (in seconds) on the X-axis. Three distinct periods of 10, one second samples are represented in charts 510, 520, 530, during the disinfection cycle, representing different regions of the main graph. The charts 510, 520, 530 show the time-temperature value contribution for each second according to the temperature sensed during the 1 second intervals.

In chart 510, the 10, one second samples are taken after approximately 50 seconds. During the 10 seconds, the water temperature increases from 64 to 67° C. This is shown by the line graph corresponding to the water temperature Y-axis on the left hand side of the chart. The time temperature contribution at these temperatures is represented by the bars, corresponding to the time temperature Y-axis on the right hand side of the chart.

No contribution is made when the water temperature is 64° C. A relatively small contribution to the time temperature value is made when the water temperature is 65 to 67° C. This corresponds to the flat region of the main graph. Summing the values for the bars indicates that the total contribution of the 10, one second intervals is 0.296. Although these contributions are small, they are counted and do contribute to shorten the time required for sanitization. In the prior art, no credit is given for this heating phase.

In chart 520, the 10, one second samples are taken after approximately 140 seconds. During the 10 seconds, the water temperature increases from 79 to 82° C. This is shown by the line graph corresponding to the water temperature Y-axis on the left hand side of the chart. The time temperature contribution at these temperatures is represented by the bars, corresponding to the time temperature Y-axis on the right hand side of the chart. Note the difference in scale of the time temperature Y-axis of chart 520 to chart 510.

Increasing contributions to the time temperature value are made as the water temperature increases from 79 to 82° C. This corresponds to the steadily increasing region of the main graph. Summing the values for the bars indicates that the total contribution of the 10, one second intervals is 12.056.

In chart 530, the 10, one second samples are taken after approximately 420 seconds. During the 10 seconds, the water temperature increases from 83 to 86° C. This is shown by the line graph corresponding to the water temperature Y-axis on the left hand side of the chart. The time temperature contribution at these temperatures is represented by the bars, corresponding to the time temperature Y-axis on the right hand side of the chart. Note the difference in scale of the time temperature Y-axis of chart 530 to charts 510 and 520.

Greatly increasing contributions to the time temperature value are made as the water temperature increases from 83 to 86° C. This corresponds to the steep region of the main graph. Summing the values for the bars indicates that the total contribution of the 10, one second intervals is 30.282. Counting the actual contribution to sanitization for the periods above 80° C. rather than treating these as the same as 80° C. considerably shortens the required time.

The charts are exemplary in nature only, and different time, temperature and associated time-temperature values are possible, and indeed envisaged.

One second intervals have been chosen as a reasonable sampling rate. The sampling interval could be longer or shorter. A longer sampling interval would preferably be associated with a steady temperature profile, whilst a shorter temperature cycle would preferably be associated with greater processing power.

In alternate embodiments of the liquid sanitizer, the processor may be programmable. Therefore the threshold temperature may be set manually. For example the threshold temperature may be set to a temperature between 55° C. and 65° C. The overall heating time may be set manually. For example, the heating time may be set to 8, 9 or 10 minutes. In this case the processor 230 calculates the necessary temperature profile over the heating time to ensure the volume of water receives a sanitizing dose.

The invention claimed is:

1. A method of sanitizing a hemodialysis, hemodiafiltration or hemofiltration dialysis machine, the method comprising the steps of:
   providing a circulating sanitization circuit, in or connected to the dialysis machine, the sanitization circuit including a tank;
   filling the tank with a volume of liquid, the volume of liquid constituting a specific liquid batch for circulation around the sanitization circuit;
   sensing a temperature of the volume of liquid with a sensor;
   heating the volume of liquid from an initial temperature to exceed a threshold temperature;
   pumping the volume of liquid around the sanitization circuit;
   maintaining the volume of liquid above the threshold temperature;
   once the threshold temperature has been exceeded, periodically determining a time-temperature value for the volume of liquid based on periodic sampling of the temperature of the volume of liquid at least at a location representing a lowest possible temperature of the volume of liquid in the circuit;

a processor calculating a cumulative time-temperature value by summing the determined time-temperature values;

the processor providing a feedback loop to moderate the heating of the volume of liquid while still maintaining the volume of liquid above the threshold temperature; and the processor providing an output signal once the cumulative time-temperature value has reached a level indicative of a sanitizing dose.

2. The method according to claim 1 wherein the determining step comprises using a look-up table to generate the time-temperature values.

3. The method according to claim 1, further comprising: setting a target cumulative time-temperature value; and wherein the output signal providing step comprises providing the output signal once the target cumulative time-temperature value is reached.

4. The method according to claim 1, wherein the output signal causes an audible or a visual alarm.

5. The method according to claim 1 wherein the output signal automatically causes termination of the heating of the volume of liquid.

6. The method according to claim 1, further comprising the step of maintaining the volume of liquid below an upper temperature.

7. The method according to claim 6, wherein the upper temperature is between 70° C. and 99° C.

8. The method according to claim 6 comprising the further step of setting the upper temperature.

9. The method according to claim 1, comprising the further step of setting the threshold temperature.

10. The method according to claim 1, comprising the further step of setting an overall heating time.

11. The method according to claim 1, wherein the threshold temperature is between 55° C. and 65° C.

12. The method according to claim 1, wherein the sensing of temperature is conducted with the sensor and at least one additional sensor comprises multiple temperature sensors.

13. The method according to claim 1, wherein the cumulative time-temperature value $A_0$ is calculated according to $$A_0 = \sum 10^{[\frac{(T-80)}{z}]} dt$$

where:
an A value is an equivalent time in seconds at 80° C. to give a disinfection effect, z is a change in temperature required to change the A value by a factor of 10, and $A_0$ is the A value when z is 10° C.;
dt is a chosen time interval, in seconds;
T is an average temperature over a time interval dt of the volume of liquid in ° C.; and
$A_0$ is a summation for all of the dt intervals.

14. The method according to claim 13, where the $A_0$ value indicative of a sanitizing dose is equal to 1800.

15. The method according to claim 1, further comprising:
the processor calculating whether there is sufficient thermal energy in the volume of liquid to remain above the threshold temperature long enough to ensure that the sanitizing dose will be reached; and
discontinuing further heating of the volume of liquid once there is sufficient thermal energy in the volume of liquid to remain above the threshold temperature long enough to ensure that the sanitizing dose will be reached.

16. A hemodialysis, hemodiafiltration or hemofiltration dialysis machine, the dialysis machine comprising:
a circulating sanitization circuit comprising a tank for receiving a volume of liquid, the volume of liquid constituting a specific liquid batch for circulation around the sanitization circuit;
a sensor arranged to sense a temperature of the volume of liquid, the sensor arranged on the circuit on a return line adjacent the tank;
a heater located in the tank and arranged to heat the volume of liquid from an initial temperature to exceed a threshold temperature, and to maintain the volume of liquid above the threshold temperature; and
a processor, wherein the processor is configured to determine a time-temperature value for the volume of liquid periodically once the threshold temperature has been exceeded, to calculate a cumulative time-temperature value by summing the time-temperature values that are determined periodically for the volume of liquid, to provide a feedback loop to moderate the heating of the volume of liquid while still maintaining the volume of liquid above the threshold temperature, and to provide an output signal once a cumulative time-temperature value indicative of a sanitizing dose is reached.

17. The dialysis machine of claim 16, further comprising a cartridge that comprises a path that is part of the circulating sanitization circuit.

18. The dialysis machine of claim 17, further comprising a door that allows reception of the cartridge in the dialysis machine liquid sanitiser.

19. The dialysis machine of claim 16, further comprising a pneumatic pump to pump the volume of liquid through the circulating sanitization circuit.

20. The dialysis machine of claim 16, wherein the processor is programmable to alter at least one of the threshold temperature and the cumulative time-temperature value indicative of the sanitizing dose being reached.

21. The dialysis machine of claim 16, wherein the processor determines the cumulative time-temperature value $A_0$ according to:

$$A_0 = \sum 10^{[\frac{(T-80)}{z}]} dt$$

where:
an A value is an equivalent time in seconds to give a disinfection effect at 80° C., z is a change in temperature required to change the A value by a factor of 10, and $A_0$ is the A value when z is 10° C.;
dt is a chosen time interval, in seconds;
T is an average temperature over a time interval dt of the volume of liquid in ° C.; and
$A_0$ is a summation for all of the dt intervals.

22. The dialysis machine of claim 21 wherein the $A_0$ value indicative of the sanitizing dose being reached is 1800.

23. The dialysis machine of claim 16, wherein the processor is configured to set a target cumulative time-temperature value and to provide the output signal once the target cumulative time-temperature value is reached.

24. The dialysis machine of claim 16, further comprising:
a main body;

the circulating sanitization circuit including the tank, the sensor, the heater, and the processor being located wholly within the main body.

25. The dialysis machine of claim 16, wherein the processor is configured to perform at least one of the following: maintaining the volume of liquid below an upper temperature, setting an upper temperature, setting the threshold temperature, and setting an overall heating time.

26. The dialysis machine of claim 16, wherein the heater comprises heating elements disposed in the tank.

27. A method of sanitizing a hemodialysis, hemodiafiltration or hemofiltration dialysis machine, the method comprising the steps of:

provic a circulating sanitization circuit, in or connected to the dialysis machine, the sanitization circuit including a tank;

filling the tank with a volume of liquid, the volume of liquid constituting a specific liquid batch for circulation around the sanitization circuit;

sensing a temperature of the volume of liquid with a sensor;

heating the volume of liquid from an initial temperature to exceed a threshold temperature;

pumping the volume of liquid around the sanitization circuit;

maintaining the volume of liquid above the threshold temperature;

once the threshold temperature has been exceeded, periodically determining a time-temperature value for the volume of liquid based on periodic sampling of the temperature of the volume of liquid at least at a location representing a lowest possible temperature of the volume of liquid in the circuit; and a processor calculating a cumulative time-temperature value by summing the determined time-temperature values, and leveraging temperatures in excess of the threshold temperature to determine as soon as the cumulative time-temperature value has reached a level indicative of a sanitizing dose.

* * * * *

UNITED STATES PATENT AND TRADEMARK OFFICE
CERTIFICATE OF CORRECTION

PATENT NO. : 10,543,305 B2
APPLICATION NO. : 15/315114
DATED : January 28, 2020
INVENTOR(S) : Clive Buckberry, Keith Heyes and Eduardo Esser It is certified that error appears in the above-identified patent and that said Letters Patent is hereby corrected as shown below:

In the Claims

In Column 9, Line 41, delete "comprises multiple temperature sensors".

In Column 10, Line 35, delete "liquid santiser".

Signed and Sealed this
Tenth Day of March, 2020

Andrei Iancu
*Director of the United States Patent and Trademark Office*